US005958719A

United States Patent [19]
Ullrich et al.

[11] Patent Number: 5,958,719
[45] Date of Patent: Sep. 28, 1999

[54] METHOD FOR THE DETERMINATION OF THE ACTIVITY OF SPECIFIC PHOSPHOTYROSINE PHOSPHATASES AND SPECIFIC EFFECTORS THEREOF IN INTACT CELLS

[75] Inventors: Axel Ullrich, Munich; Sylvia-Annette Böhmer; Frank Böhmer, both of Dorndorf; Axel Obermeier, Munich, all of Germany

[73] Assignee: Max-Planck Gesellschaft Zur Foderung der Wissenschaften E.V., Munich, Germany

[21] Appl. No.: 08/544,427

[22] Filed: Nov. 6, 1995

[51] Int. Cl.$^6$ .............................. C12Q 1/42; A61K 38/18
[52] U.S. Cl. ............................................. 435/21; 530/399
[58] Field of Search ................................ 435/21; 530/399

[56] References Cited

FOREIGN PATENT DOCUMENTS 0165430 12/1985 European Pat. Off. .
3704389 8/1988 Germany .

OTHER PUBLICATIONS

Barinaga, M., "Neurotrophic Factors Enter the Clinic," *Science* 264:772–774 (1994).
Bohmer et al., "The dephosphorylation characteristics of the receptors for epidermal growth factor and platelet derived–growth factor in Swiss 3T3 cell membranes suggest differential regulation of receptor signalling by endogenous protein–tyrosine phosphatases," *FEBS Letters* 331:276–280 (1993).
Charbonneau and Tonks, "1002 Protein Phosphatases?" *Ann. Rev. Cell. Biol.* 8:463–493 (1992).
Debono et al., "Synthesis and Characterization of Halogenated Derivatives of the Ionophore A23187: Enhanced Calcium Ion Transport Specificity by the 4–Bromo Derivative," *Biochemistry* 20:6865–6872 (1981).
Faure et al., "The Dephosphorylation of Insulin and Epidermal Growth Factor Receptors," *J. Biol. Chem.* 267:11215–11221 (1992).
Goldstein, B., "Protein–Tyrosine Phosphatases and the Regulation of Insulin Action," *J. Cell. Biol.* 48:33–42 (1992).
Hosang et al., "Both Homodimeric Isoforms of PDGF (AA and BB) Have Mitogenic and Chemotactic Activity and Stimulate Phosphoinositol Turnover," *J. Cell. Physiol.* 140:558–564 (1989).
Levitzki, "Tyrphostins: tyrosine kinase blockers as novel antiproliferative agents and dissectors of signal transduction," *FASEB Journal* 6:3275–3282 (1992).

Obermeier et al., "Neuronal differentiation signals are controlled by nerve growth factor receptor/Trk binding sites for SHC and PLCγ," *EMBO J.* 13:1585–1590 (1994).
Ohmichi et al., "Inhibition of the Cellular Actions of Nerve Growth Factor by Stauroporine and K252A Results from the Attenuation of the Activity of the trk Tyrosine Kinase," *Biochemistry* 31:4034–4039 (1992).
Tapley et al., "K252a is a selective inhibitor of the tyrosine protein kinase activity of the trk family of oncogenes and neurotrophin receptors," *Oncogene* 7:371–381 (1992).
Mooney and Bordwell, "Differential Dephosphorylation of the Insulin Receptor and Its 160–kDa Substrate (pp 160) in Rat Adipocytes," *J. Biol. Chem.* 267:14054–14060 (1992).
Pot and Dixon, "A thousand and two protein tyrosine phosphatases," *Biochem. Biophys. Acta* 1136:35–43 (1992).
Ross, "The pathogenesis of atherosclerosis: a perspective for the 1990s," *Nature* 362:801–809 (1993).
Rubin et al., "Expression of Platelet–Derived Growth Factor Receptors is Induced on Connective Tissue Cells During Chronic Synovial Inflammation," *Scand. J. Immunol.* 27:285–294 (1988).
Shaw et al., "Pathogenesis of Pulmonary Fibrosis in Interstitial Lung Disease," *Am. Rev. Resp. Dis.* 143:167–173 (1991).
Snider, W.D., "Functions of the Neurotrophins during Nervous System Development: What the Knockouts Are Teaching Us," *Cell* 77:627–638 (1994).
Swarup et al., "Inhibition of Membrane Phosphotyrosyl–Protein Phosphatase Activity by Vanadate," *Biol and Biophys. Research Communications* 107:1104–1109 (1982).
Ullrich and Schlessinger, "Signal Transduction by Receptors with Tyrosine Kinase Activity," *Cell* 61:203–212 (1990).

*Primary Examiner*—Gary L. Kunz
*Attorney, Agent, or Firm*—Lyon & Lyon LLP

[57] ABSTRACT

For the determination of the activity of a specific protein tyrosine phosphatase (PTPase) in intact cells one incubates intact cells which contain a substrate of the specific PTPase, if desired after stimulating the substrate phosphorylation, with a substance which can penetrate into the intact cells and can selectively inhibit phosphorylation of the substrate, the degree of phosphorylation of the substrate is measured, if desired several times, at various time points and the activity of the specific PTPase is determined from the measured degree of phosphorylation of the substrate. An additional measurement is carried out in the presence of a test substance to determine effectors of the specific PTPase and the effector action of the test substance is determined by comparing the degrees of phosphorylation.

15 Claims, 3 Drawing Sheets

METHOD FOR THE DETERMINATION OF THE ACTIVITY OF SPECIFIC PHOSPHOTYROSINE PHOSPHATASES AND SPECIFIC EFFECTORS THEREOF IN INTACT CELLS

The present invention concerns a method for determining the activity of protein tyrosine phosphatases and for identifying effectors thereof.

The phosphorylation of cellular proteins at tyrosine residues is a general underlying principle for the regulation or control of cellular processes and conditions. This mechanism is for example of particular importance in the transmission of signals in cells and in the regulation of cell proliferation and differentiation (Ullrich and Schlessinger (1990)). Proteins which are specifically phosphorylated in response to a particular signal comprise proteins on the cell surface such as receptors for growth factors, hormones etc. as well as intracellular proteins.

The "setting" of the phosphorylation level is achieved by protein tyrosine kinases (PTK) and their counterparts the protein tyrosine phosphatases (PTPases) which have only been characterized in detail in recent years (Charbonneau and Tonks (1992); Pot and Dixon (1992)).

Due to the importance of protein phosphorylation at tyrosine residues for cell proliferation and differentiation, much interest has been shown for these two classes of enzymes. Determination of the activity of specific PTKases and PTPases in vivo enables for example valuable conclusions to be drawn about the involvement of protein tyrosine phosphorylation in pathological proliferative processes; natural and synthetic effectors of both classes of enzymes are active substances with a high potential medical relevance for influencing such processes.

Common methods for determining enzyme activities or for identifying effectors thereof known from the state of the art comprise the identification and isolation of the respective enzyme and in vitro investigations. However, the identification of specific PTPases such as the PTPases for the PDGF receptor or the NGF receptor is difficult and has not yet succeeded. Therefore at present it is not possible to construct a test system for these PTPases which is based on isolated enzymes. In addition the specificity of the PTPases is apparently determined to a high degree by their spatial vicinity to their respective substrates in the cell. Isolation of PTPases leads at least partially to a loss of such specificities and thus experiments on isolated PTPases could possibly give a wrong picture. In an analogous manner the specificity of effectors is often different in a cellular context than in isolated systems.

In addition methods are known from the state of the art which enable the activity of specific PTPases to be determined in situ but a prerequisite for these methods is that it is possible to isolate the respective substrate for the specific PTKases and PTPases and to analyse the phosphotyrosine content of this substrate. When $^{32}P$ is used such methods comprise the addition of non-radioactive ATP to the mixture and subsequent monitoring of the phosphorylation/dephosphorylation of the substrate (Swarup et al. (1982); B öhmer et al. (1993); Faure et al. (1992)) or the inhibition of PTK by chelators of essential divalent cations for the kinase reaction, such as EDTA and monitoring the phosphotyrosine content. A disadvantage of these known systems is their low specificity since they target all tyrosine kinases in a test sample without distinctions being made which makes it impossible to reach conclusions about a specific effect. A further major disadvantage is that neither chelators nor ATP can rapidly permeate into cells so that the use of these methods requires prior cell permeabilization or lysis of the cells (Mooney and Bordwell (1992)). Consequently these methods are unsuitable for correctly determining the in vivo activity of specific PTPases in an intact cell.

It is therefore the object of the present invention to provide a method for the measurement of specific PTPase activities which at least partially avoids the known disadvantages from the state of the art and which can be carried out on an intact cell.

This object is achieved by a method for the determination of the activity of a specific protein tyrosine phosphatase (PTPase) in intact cells, which is characterized in that (a) intact cells which contain a substrate of the PTPase to be determined are incubated, if desired after stimulating substrate phosphorylation, with an effective concentration of at least one substance which can penetrate into the intact cell and can selectively inhibit the phosphorylation of the substrate, (b) the degree of phosphorylation of the substrate is measured after a given incubation period, (c) if desired, step (b) is repeated at least once and (d) the activity of the specific PTPase is determined from the measured degree of phosphorylation of the substrate.

Inhibition of substrate phosphorylation by the substance can be caused by various mechanisms of action such as by interaction with the phosphorylation site of the substrate or by interaction with a specific protein tyrosine kinase. In a particular embodiment the substance is a specific PTK inhibitor. In the following the effect of this substance is usually described as an inhibition of the specific PTK. However, the present invention is also intended to encompass other mechanisms of action.

The ongoing phosphorylation of the specific substrates is stopped in vivo by the inhibition of PTK thus revealing the action of specific PTPases which dephosphorylate these substrates. An important advantage of the method according to the invention is that the substrate phosphorylation is selectively inhibited which reduces side-effects to a minimum that would have been unavoidable when using hitherto conventional unselective inhibitors. A further advantage of the method according to the invention compared to systems known from the state of the art is that the specific PTK inhibitors can rapidly permeate into intact cells. A cell permeabilization is not necessary in this process and thus the in vivo situation is left intact except for the specifically blocked PTK.

In order to carry out the method according to the invention cells which express the substrate are incubated for a given period with at least one specific PTK inhibitor. Afterwards the cells are preferably disrupted and the degree of phosphorylation of the substrate is determined. In order to determine the in vivo activity of PTPases at least two measurements after different incubation periods are preferably carried out to determine the time course of substrate dephosphorylation. In order to avoid errors in the measured results it is usually necessary to previously separate the substrate from other interfering components. Methods for this are known to a person skilled in the art and comprise for example immunoprecipitation etc.. The determination of the degree of phosphorylation of the substrate can be carried out by methods known in the art, for example by using anti-phosphotyrosine antibodies.

In principle all prokaryotic and eukaryotic cells that express the substrate are suitable as cells; mammalian cells and especially human cells being preferred due to their medical relevance. For reasons of simpler handling conventional cell lines such as Swiss 3T3 or PC12 cells are generally used.

In order to improve the measuring accuracy it is generally preferable to ensure that the substrate for the tested PTPase is present in a substantially phosphorylated form. In cases in which the substrate is only phosphorylated as a result of a particular signal, it is usually preferable to trigger the effect of this signal. For example in the case of surface receptors which are only phosphorylated by the specific PTK after binding of a ligand, an incubation with the respective ligand can be carried out before addition of the PTK inhibitor. In other cases it may also be preferable to carry out a pre-incubation with inhibitor followed by stimulation by ligands in particular when only a qualitative result is wanted by comparison with a control determination in the absence of an inhibitor. In yet other cases it may be preferable not to stimulate when for example the substrate is already phosphorylated due to the particular type of cell used.

Any substance in an effective concentration that selectively inhibits the phosphorylation of the substrate or a specific PTK of the substrate and which can penetrate into intact cells can be used as the selective PTK inhibitor. An effective concentration is understood as that concentration which achieves at least a substantial inactivation of the specific substrate phosphorylation and at which at the same time no side-effects can be observed which would impair the measured result or/and would be toxic for the cells. In general concentrations in the range of about 0.1 to 100 μM are used. The inhibitor substance is selected with respect to the substrate or of the PTK to be inhibited. PTK inhibitors are known from the state of the art (Levitzky (1992); Burke (1992)). The substances mentioned in the description or which are used in the examples of the present invention encompass for example the quinoxaline derivatives AG1295, AG1296 as well as the staurosporine derivative K252a having the following structural formulae:

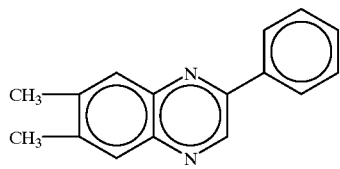
AG1295

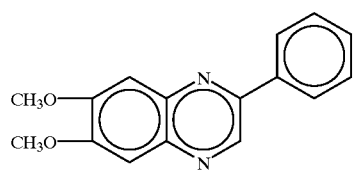
AG1296

-continued

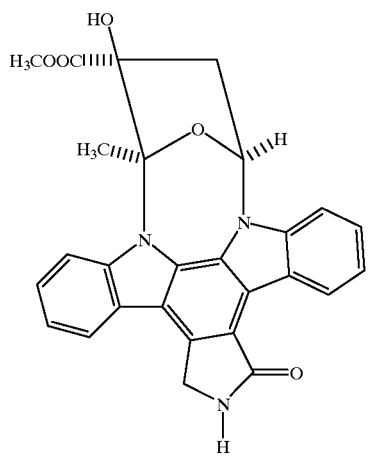
K252a

The specific PTK that is selectively inhibited when the method according to the invention is carried out does not necessarily represent an independent enzyme. The PTK can for example be a protein associated with the substrate or a subunit of the substrate so that the phosphorylation is an autophosphorylation.

The substrate of the PTPase to be determined can be any cellular protein and it is only important that this protein is phosphorylated by a specific PTK and is dephosphorylated by specific PTPases. Such substrates comprise for example intracellular proteins such as nuclear proteins or membrane-associated proteins as well as integral membrane proteins e.g. on the cell surface. It was found that cell surface receptors such as e.g. receptors for a growth factor such as the NGF receptor, PDGF receptor, KIT/SCF receptor, KD receptor, EGF receptor and insulin receptor are extremely well suited as a substrate for the method according to the invention.

A suitable combination of protein and PTK inhibitor encompasses for example the use of the PDGF receptor as a substrate and the PTK inhibitor AG1295 and/or AG1296. This combination is thus suitable for determining the activity of PTPases which act on the PDGF receptor or for finding effectors of these PTPases. Another preferred combination encompasses a NGF receptor and K252a as the PTK inhibitor which enable the activity of PTPases acting on a NGF receptor or effectors thereof to be determined.

In a particular embodiment the method of the present invention enables effectors of the specific PTPase to be identified. For this the activity of the specific PTPase is determined according to the method of the invention and an additional determination is carried out in the presence of a test substance. By comparing the degrees of phosphorylation of the substrate with and without test substance it is possible to determine the effect of the test substance on the activity of the specific PTPase.

Such effectors have an extremely high medical relevance due to their potential capability of influencing pathological proliferative and differentiation processes.

It is for example assumed that PDGF plays a key role in undesired hyperproliferations in certain tumours, in arteriosclerosis, arthritis and fibroses (Heldin and Westermark (1991); Ross, (1993); Rubin et al. (1988); Shaw et al. (1991)). Activators of the PDGF receptor PTPases which negatively regulate this signal path can be used as specific cytostatic agents to influence these pathological processes. NGF and related neurotrophic factors play a decisive role in neuronal differentiation (Snider (1994)). An inadequate activity of this differentiation-inducing regulation is probably the basis of various neurodegenerative diseases (Barinaga (1994)). Inhibitors of the PTPases which negatively regulate the NGF signal path are potential neurotrophic substances and can be used to treat such diseases. Non-insulin dependent diabetes mellitus (NIDDM) is a similar situation which is the result of a hypofunction of the insulin receptor (Goldstein (1992)). Inhibitors of the PTPase (s) directed towards the insulin receptor have an insulin-mimetic function in animal models but up to now only relatively toxic and unspecific substances of this kind are known. When specific inhibitors of the insulin receptor PTK become available, the method according to the invention could also be used to find specific inhibitors of the insulin receptor PTPases and thus selective insulin-mimetics.

The present invention in addition concerns the use of the effectors identified by the method according to the invention as activators or inhibitors of specific PTPases. It has for example been found that certain ionophores can selectively influence the activity of specific PTPases. Such ionophores are natural or synthetic substances which transport ions such as $Na^+$, $K^+$, $Ca^{2+}$ and $Mg^{2+}$ through membranes. Channel formers as well as mobile carriers are known as ionophores it is, however, assumed that a selective action is mainly mediated by the mobile carriers. In a preferred embodiment of the invention an ionophore is used as the effector which transports divalent ions and in particular $Ca^{2+}$ and/or $Mg^{2+}$ ions such as e.g. the ionophore A23187, 5-(methylamino)-2-[[3,9,11-trimethyl-8-[1-methyl-2-oxo-(1H-pyrrol-2-yl) ethyl]-1,7-dioxaspiro[5,5]undec-2-yl]methyl-4-benoxazolcarboxylic acid

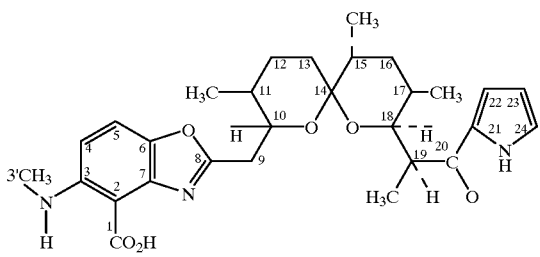

or derivatives thereof (Debono et al. (1981)). A23187 acts as an activator of PTPases which specifically dephosphorylate the PDGF receptor. The action of A23187 is shown in example 3.

Yet another subject matter of the present invention is to provide a pharmaceutical composition for influencing the effect of PTPases in intact cells which is characterized in that it contains an ionophore as the active substance and if desired common auxiliary substances, diluents and carriers.

In this connection the active substance is present in an amount which causes the desired inhibition of the specific PTPase and which essentially causes no toxic side-effects. Although the dose is dependent on the respective active substance, it can in general be assumed that an active amount is about 0.01 to 100 mg/kg body weight. The pharmaceutical composition is administered by a suitable method. Such forms of administration are known to a person skilled in the art such as oral, subcutaneous, intravenous, intramuscular administration etc.. In the composition the active substance is present in a form which enables transport to the target tissue. Depending on the active substance and the form of administration, such forms comprise for example aqueous or oily solutions, liposomes, depot preparations etc..

In a preferred embodiment the active substance of the pharmaceutical composition is an ionophore which transports $Mg^{2+}$ and/or $Ca^{2+}$ and in a particularly preferred embodiment the pharmaceutical composition contains the calcium ionophore A23187 for activating PTPase activity directed towards the PDGF receptor.

The method according to the invention is further elucidated by the following examples in conjunction with the figures.

EXAMPLE 1

Figure 1:
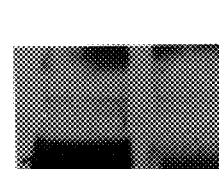
FIG. 1 shows the inhibition of the PDGF receptor PTK by AG1296.
Figure 2:
FIG. 2 shows the activity of the PDGF receptor-PTPases when using AG1296.
Figure 3:
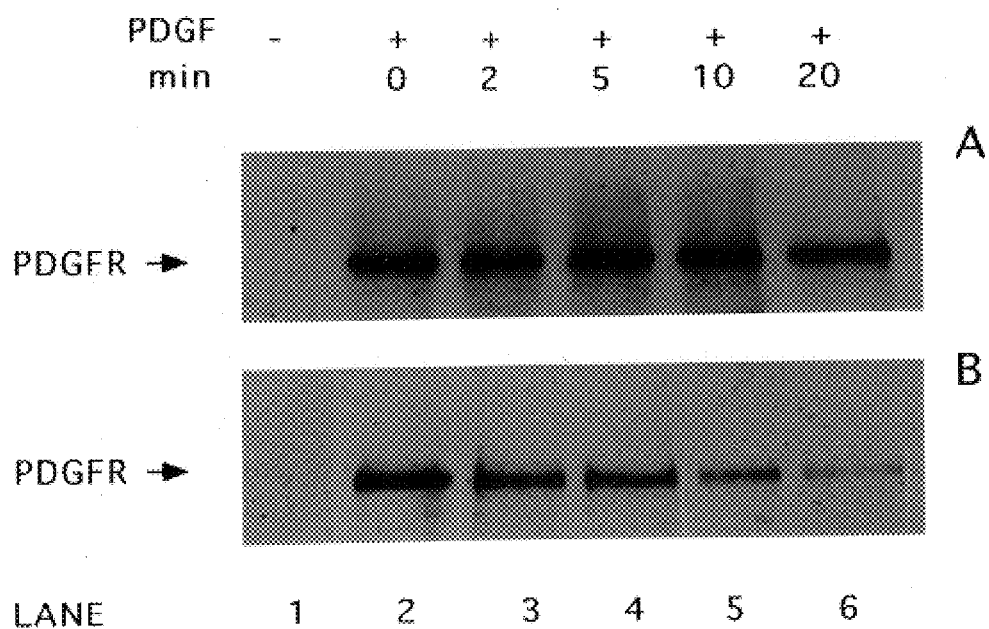
FIG. 3 shows an embodiment of the method according to the invention in Swiss 3T3 cells.

Measurement of the PDGF receptor-directed PTPase(s) in Swiss 3T3 cells with the aid of a specific inhibitor of the PDGF receptor-PTK Swiss 3T3 fibroblasts (mouse) express PDGFα and PDGFβ receptors on the cell surface (Hosang et al. (1989)). Stimulation of the cells with PDGF leads to a rapid autophosphorylation of these receptors at tyrosine residues. This autophosphorylation can be detected in immunoblots using anti-phosphotyrosine antibodies after immunoprecipitation of the receptors and can be detected in unfractionated cell lysates. The autophosphorylated receptors are rapidly dephosphorylated by PDGF receptor-directed PTPase(s) (Bohmer et al. (1993)). The identity of the cellular PTPases which catalyse this reaction is not known. A highly specific inhibitor for the PDGF receptor PTK (AG1296) already completely inhibits its activity after a very short treatment of the cells (2 min) (FIG. 1). In isolated membranes of Swiss 3T3 cells the inhibitor does not influence the activity of the PTPase(s) for the autophosphorylated PDGF receptor present in the membranes (FIG. 2). If the inhibitor is added to cells after activation of the PDGF receptor PTK, the dephosphorylation of the PDGF receptor can be monitored over time. (FIG. 3).

Inhibition of the PDGF receptor PTK by the specific inhibitor AG 1296 (FIG. 1)

Confluent, resting Swiss 3T3 cells were incubated as stated for various periods in serum-free cell culture medium without supplements (lanes 1, 2) or with the PDGF receptor PTK inhibitor AG1296 (final concentration 50 μM) (lanes 3–6). Then human recombinant PDGF-BB (final concentration 100 ng/ml) (lanes 2–6) or the corresponding solvent (lane 1) was added and the incubation was continued for 5 minutes. A cell extract was prepared by standard methods and comparable amounts of the extracts were analysed by means of SDS-PAGE and immunoblotting with anti-phosphotyrosine antibodies. The PDGF-induced autophosphorylation of the receptor is already completely suppressed by incubating the cells for 2 min with AG1296.

AG1296 does not inhibit the PDGF receptor-directed PTPase(s) (FIG. 2)

Isolated Swiss 3T3 cell membranes (10 μg protein per lane) were treated for 20 minutes on ice with PDGF (2 μg/ml). The activated PDGF receptor PTK was then autophosphorylated by adding 3 mM (final concentration) ATP. The kinase reaction was inhibited by addition of 10 mM EDTA. At the same time AG1296 (50 μM) (B) or the corresponding solvent (DMSO) (A) was added. The phosphotyrosine content of the PDGF receptor was measured in a similar manner to that described in FIG. 1 immediately after addition of the agents (0 min) or after 30 min incubation. The substantially weakened signal after 30 min is due to the dephosporylating action of the PTPase(s). AG1296 does not influence this dephosphorylation.

Figure 4:
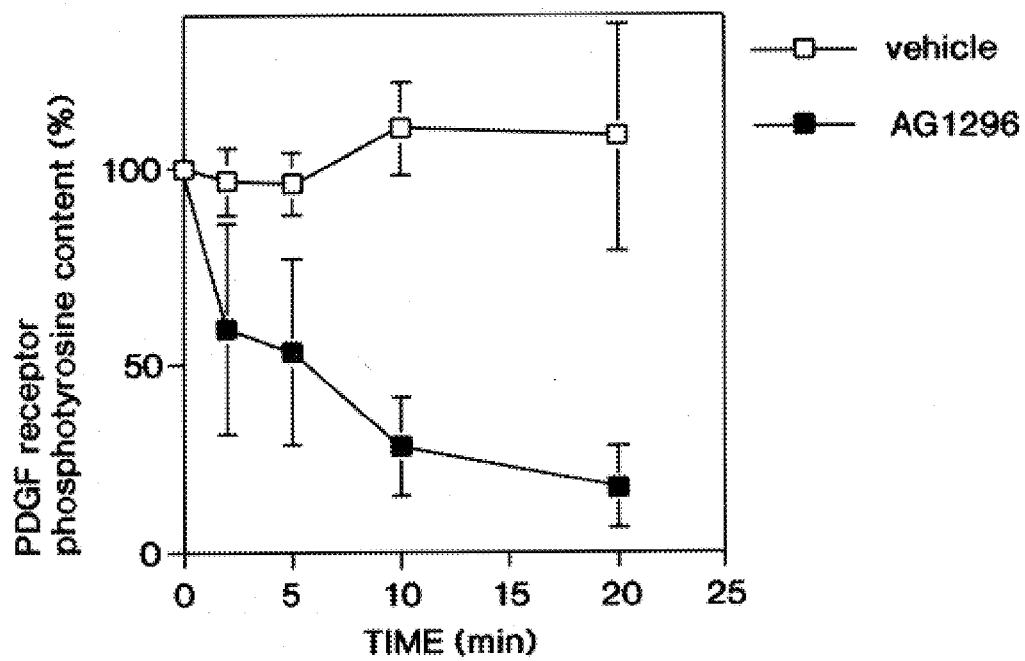
FIG. 4 shows a graphical evaluation of the experiment of FIG. 3.

Treatment of intact Swiss 3T3 cells with AG1296 enables detection of the activity of PDGF receptor-directed PTPase(s) in vivo (FIGS. 3 and 4)

Swiss 3T3 cells were treated in serum-free medium with PDGF (FIG. 3, lanes 2–6) or the corresponding solvent (FIG. 3, lane 1). After 5 minutes stimulation AG1296 (50 μM, FIG. 3B) or the corresponding solvent (DMSO, FIG. 3 A) was added. The phosphotyrosine content of the PDGF receptor was examined in the cells thus treated at the stated various time points. Whereas in the DMSO-treated cells the phosphotyrosine content of the stimulated PDGF receptor remains approximately constant over the incubation period (equilibrium of PTK and PTPase reaction), the phosphotyrosine content of the receptors in the cells treated with the PTK inhibitor continuously decreases. This decrease is caused by the activity of the PDGF receptor-directed PTPase in the intact cells. A graphic evaluation is shown in FIG. 4.

The identity and the constant concentration over the experimental period of the PDGF receptor was ascertained by immunoprecipitation in control experiments (not shown).

EXAMPLE 2

Measurement of the NGF receptor (Trk)-directed PTPase(s) in PC12 cells with the aid of a specific inhibitor of the NGF receptor PTK PC 12 cells (rat pheochromocytoma cells) which overexpress NGF receptors (Trk A) (Obermeier et al. (1994)) were used for the experiments shown. Stimulation of the cells with NGF leads to a rapid autophosphorylation of these receptors at tyrosine residues. This autophosphorylation can be detected in immunoblots using anti-phosphotyrosine antibodies after immunoprecipitation of the receptors. The identity of the cellular PTPases which dephosphorylate autophosphorylated NGF receptors is not known. The staurosporine derivative K252a has been described as a specific inhibitor of the NGF receptor PTK and also of the PTK activity of other neurotrophin receptors (Ohmichi et al (1992); Tapley et al (1992)). Analogously to the experiments described in example 1 it was found that K252a already completely inhibits the activity of Trk receptor PTK after a short treatment of the cells (FIG. 4). If the inhibitor is added to cells after activation of Trk, the very rapid dephosphorylation of the NGF receptor can be measured (FIG. 5).

The constant concentration of the NGF receptor during the experimental period was ascertained in control experiments (not shown).

Figure 5:
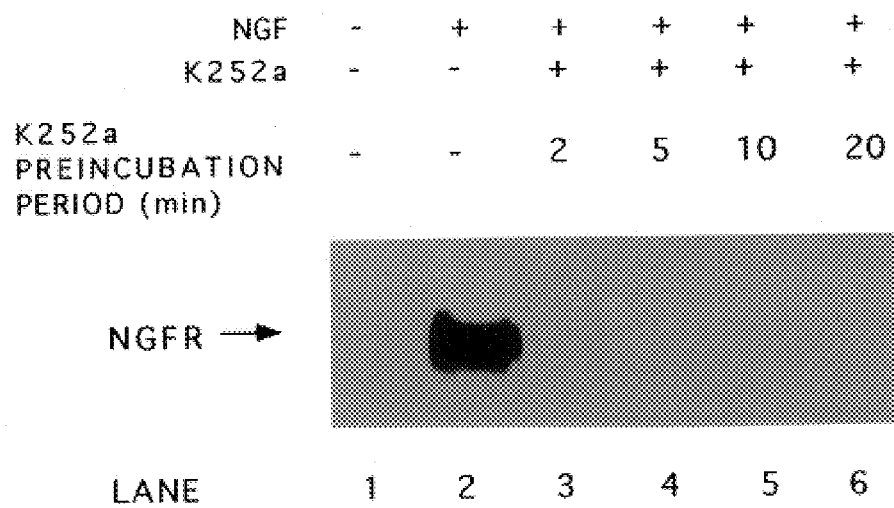
FIG. 5 shows the inhibition of the NGF receptor PTK by K252a, FIG. 6 shows another embodiment of the method according to the invention in PC12 cells.

Inhibiton of the NGF receptor PTK (Trk) by the specific inhibitor K252a (FIG. 5)

PC12 cells that overexpress TrkA were incubated as stated for various periods in serum-free cell culture medium without supplements (lanes 1, 2) or with the NGF receptor PTK inhibitor K252a (final concentration 1 μM) (lanes 3–6). Then NGF (final concentration 150 ng/ml) (lanes 2–6) or the corresponding solvent (lane 1) was added and the incubation was continued for 10 minutes. A cell extract was prepared by standard methods, the NGF receptors were immunoprecipitated with a specific antibody and comparable amounts of the immunoprecipitate were analysed by means of SDS-PAGE and immunoblotting with anti-phosphotyrosine antibodies. The NGF-induced autophosphorylation of the receptor is already completely suppressed by incubating the cells for 2 min with K252a.

Figure 6:
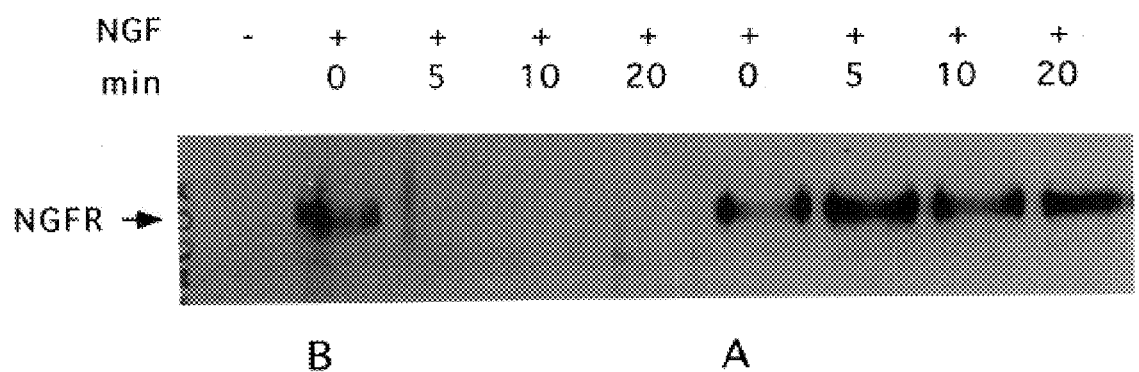

Treatment of intact PC12 cells with K252a enables detection of the activity of NGF receptor-directed PTPase(s) in vivo (FIG. 6)

PC12 cells transfected with TrkA were treated in serum-free medium with NGF (lanes 2–6) or the corresponding solvent (lane 1). After a 10 minute stimulation, K252a (1 μM, B) or the corresponding solvent (DMSO, A) was added. At the stated various time points the cells treated correspondingly were tested as described in FIG. 1 and the phosphotyrosine content of the NGF receptors was examined. Whereas the phosphotyrosine content of the stimulated NGF receptor remains approximately constant over the incubation period in the DMSO-treated cells (equilibrium of PTK and PTPase reaction), the phosphotyrosine content of the receptor in the cells treated with the PTK inhibitor decreases significantly. This decrease is caused by the activity of the NGF receptor-directed PTPase in the intact cells.

EXAMPLE 3

The test according to the invention for the PDGF receptor-directed PTPase(s) enables detection of PTPase effectors Pretreatment of Swiss 3T3 cells with potential effectors of the PDGF receptor-specific PTPases accelerates (PTPase activators) or retards (PTPase inhibitors) the dephosphorylation. The effect measured in this way of the known unspecific PTPase inhibitors Na orthovanadate and phenylarsine oxide and of the activator A23187 according to the invention is shown in Table 1.

Swiss 3T3 cells were treated with the effectors (or corresponding solvents) listed in Table 1. The activity of the PDGF receptor PTPase(s) was then analysed using the aforementioned test. The immunoblots were quantified by means of direct fluorescence detection (imaging system G250, Biorad) or by film exposure and densitometry (image 1.04). The relative dephosphorylation of the PDGF receptor after 5 min is stated in % in comparison to control experiments without effector (100%).

TABLE 1

| Effector | Relative PDGF receptor-directed PTPase activity (% of control) |
|---|---|
| Na orthovanadate (2 mM) | 34 |
| Phenylarsine oxide (PAO) (25 μM) | 38 |
| A 23187 (1 μM) | 161 |

Literature

Barinaga, M. (1994), Science 264, 772–774.

Böhmer, F. D., Böhmer, S. A. und Heldin, C. H. (1993), FEBS Lett. 331, 276–280.

Burke, T. R. (1992), Frugs of the Future 17, 119–131.

Charbonneau, H. und Tonks, N. K. (1992), Annu. Rev. Cell Biol. 8, 463–493.

Debono, M., Molloy, R. M., Dorman, D. E., Paschal, J. W., Babcock, D. F., Deber, C. M. und Pfeiffer, D. R. (1981), Biochemistry 20, 6865–6872.

Faure, R., Baquiran, G., Bergeron, J. J. M. und Posner, B. I. (1992), J. Biol. Chem. 267, 11215–11221.

Goldstein, B. (1992), J Cell Biochem 48, 33–42.

Heldin, C. H. und Westermark, B. (1991), CRC Crit. Rev. Oncogenesis 2, 109–124.

Hosang, M., Rouge, M., Wipf, B., Eggimann, B., Kaufmann, F. und Hunziker, W. (1989), J. Cell. Physiol. 140, 558–564.

Levitzky, A. (1992), FASEB J. 6, 3275–3282.

Obermeier, A., Bradshaw, R. A., Seedorf, K., Choidas, A., Schlessinger, J. und Ullrich, A. (1994), EMBO J 13, 1585–1590.

Ohmichi, M., Decker, S., Pang, L. und Saltiel, A. (1992), Biochemistry 31, 4034–4039.

Tapley, P., Lamballe, F. und Barbacid, M. (1992), Oncogene 7, 371–381.

Mooney, R. A. und Bordwell, K. L. (1992), J. Biol. Chem. 267, 14054–14060.

Pot, D. A. und Dixon, J. E. (1992); Biochim. Biophys. Acta 1136, 35–43.

Ross, R. (1993), Nature 362, 801–809.

Rubin, K., Terracio, L., Rönnstrand, L., Heldin, C. H. und Klareskog, L. (1988), Scand. J. Immunol. 27, 285–294.

Shaw, R. J., Benedict, S. H., Clark, R. A. und King, T. E. (1991), Am. Rev. Resp. Dis. 143, 167–173.

Snider, W. D. (1994), Cell 77, 627–638.

Swarup, G., Cohen, S. und Garbers, D. L. (1982), Biochem.Biophys.Res.Comm. 107, 1104–1109.

Ullrich, A. und Schlessinger, J. (1990), Cell 61, 203–212.

We claim:

1. A method for determining the activity of a protein tyrosine phosphatase in intact cells containing a phosphorylated substrate of the protein tyrosine phosphatase, comprising the steps of:
   (a) contacting the intact cells with an effective concentration of at least one substance which can penetrate into the intact cells and selectively inhibit the phosphorylation of the substrate for an incubation period sufficient to allow such penetration and inhibition;
   (b) measuring the degree of phosphorylation of the substrate after the incubation period; and
   (c) determining the activity of the protein tyrosine phosphatase from the measured degree of phosphorylation of the substrate.

2. The method according to claim 1, wherein, prior to step (a), the phosphorylation of the substrate is stimulated within the intact cell.

3. The method according to claim 1, wherein step (b) is repeated at least once.

4. The method according to claim 1, wherein the substance is a selective inhibitor of a protein tyrosine kinase which phosphorylates the substrate.

5. The method according to claim 4, wherein the protein tyrosine kinase is a subunit of the substrate so that the phosphorylation is an autophosphorylation.

6. The method according to claim 4, wherein the substrate is a cell surface receptor.

7. The method according to claim 6, wherein the cell surface receptor is a receptor for a growth factor.

8. The method according to claim 7, wherein the cell surface receptor is selected from the group consisting of NGF receptor, PDGF receptor, KIT/SCF receptor, KD receptor, EGF receptor and insulin receptor.

9. The method according to claim 8, wherein the substrate is a PDGF receptor and the protein tyrosine kinase inhibitor is AG 1295.

10. The method according to claim 8, wherein the substrate is a PDGF receptor and the protein tyrosine kinase inhibitor is AG 1296.

11. The method according to claim 8, wherein the substrate is a NGF receptor and the protein tyrosine kinase inhibitor is K252 A.

12. A method of screening for effectors of a specific protein tyrosine phosphatase comprising the method of claim 1 and additionally comprising the steps of:
   (a) contacting the intact cells with a test substance which is a potential inhibitor of the protein tyrosine phosphatase;
   (b) determining the degree of phosphorylation of the substrate; and
   (c) comparing the degree of phosphorylation of the substrate to the degree of phosphorylation of comparable substrate from cells which were not contacted with the test substance, wherein a difference in the measured degrees of phosphorylation indicates that the test substance is an effector of the specific protein tyrosine phosphatase.

13. The method according to claim 12, wherein the effector is an ionophore.

14. The method according to claim 13, wherein the ionophore is a calcium ionophore and/or a magnesium ionophore.

15. The method according to claim 14, wherein the ionophore is the ionophore A23187 or a derivative thereof.

* * * * *